United States Patent
Bhowmick et al.

(10) Patent No.: US 11,155,587 B2
(45) Date of Patent: Oct. 26, 2021

(54) MODULAR RESILIN-MIMETIC ELASTOMERIC PLATFORM

(71) Applicant: Pandorum Technologies Private Limited, Bangalore (IN)

(72) Inventors: Tuhin Bhowmick, Kolkata (IN); Arun Chandru Raja, Bangalore (IN)

(73) Assignee: PANDORUM TECHNOLOGIES PRIVATE LIMITED, Bangalore (IN)

( * ) Notice: Subject to any disclaimer, the term of this patent is extended or adjusted under 35 U.S.C. 154(b) by 0 days.

(21) Appl. No.: 16/349,065

(22) PCT Filed: Nov. 17, 2017

(86) PCT No.: PCT/IN2017/050538
§ 371 (c)(1),
(2) Date: May 10, 2019

(87) PCT Pub. No.: WO2018/092156
PCT Pub. Date: May 24, 2018

(65) Prior Publication Data
US 2019/0375804 A1    Dec. 12, 2019

(30) Foreign Application Priority Data
Nov. 18, 2016 (IN) .............................. 201641017212

(51) Int. Cl.
C07K 14/435 (2006.01)
C12N 15/70 (2006.01)
C12P 21/02 (2006.01)

(52) U.S. Cl.
CPC ........ *C07K 14/43563* (2013.01); *C12N 15/70* (2013.01); *C12P 21/02* (2013.01)

(58) Field of Classification Search
None
See application file for complete search history.

(56) References Cited

PUBLICATIONS

Balu et al. (Multi-responsive biomaterial and nanobioconjugates from resilin-like protein polymers Journal of materials chemistry B, Jun. 2014, vol. 2 p. 5936-5947).*
Elvin et al.: "Synthesis and properties of crosslinked recombinant pro-resilin", Nature, vol. 437, pp. 999-1002, 2005.
Li et al.: "Tunable Mechanical Stability and Deformation Response of a Resilin-Based Elastomer", Biomacromolecules, vol. 12, No. 6, pp. 2302-2310, Jun. 2011.
Int'l Search Report and Written Opinion dated Feb. 12, 2018 in Int'l Application No. PCT/IN2017/050538.

* cited by examiner

*Primary Examiner* — James H Alstrum-Acevedo
*Assistant Examiner* — Tara L Martinez
(74) *Attorney, Agent, or Firm* — Panitch Schwarze Belisario & Nadel LLP

(57) ABSTRACT

Disclosed herein is a synthetic polypeptide with "n" number of repeats of a sequence as set forth in SEQ ID NO: 1 or SEQ ID NO: 2. The synthetic polypeptide as disclosed herein is represented by an amino acid sequence selected from the group consisting of SEQ ID NO: 3, SEQ ID NO: 4, or SEQ ID NO: 5. The synthetic polypeptide of the present disclosure is used to prepare synthetic elastomeric hydrogel. Also, disclosed are the methods of preparing the synthetic polypeptide and the elastomeric hydrogel along with their uses.

16 Claims, 5 Drawing Sheets
(5 of 5 Drawing Sheet(s) Filed in Color)
Specification includes a Sequence Listing.

```
                            SEQUENCE LISTING

<160> NUMBER OF SEQ ID NOS: 8

<210> SEQ ID NO 1
<211> LENGTH: 17
<212> TYPE: PRT
<213> ORGANISM: Artificial Sequence
<220> FEATURE:
<223> OTHER INFORMATION: SEQ ID NO: 1 depicts the peptide repeat
      sequence

<400> SEQUENCE: 1

Pro Ser His Ser Tyr Ser Ala Pro Gly Gln Gly Gln Gly Asn Gly Gln
1               5                   10                  15

Gly

<210> SEQ ID NO 2
<211> LENGTH: 17
<212> TYPE: PRT
<213> ORGANISM: Artificial Sequence
<220> FEATURE:
<223> OTHER INFORMATION: SEQ ID NO: 2 depicts the peptide repeat
      sequence

<400> SEQUENCE: 2

Pro Ser Asp Ser Tyr Gly Ala Pro Gly Gln Gly Gln Gly Asn Gly Gln
1               5                   10                  15

Gly

<210> SEQ ID NO 3
<211> LENGTH: 393
<212> TYPE: PRT
<213> ORGANISM: Artificial Sequence
<220> FEATURE:
<223> OTHER INFORMATION: SEQ ID NO: 3 depicts the protein sequence of
      MODELAS1775-v2

<400> SEQUENCE: 3

Met Gly Gly Gly Gln Gly Arg Pro Ser His Ser Tyr Ser Ala Pro Gly
1               5                   10                  15

Gln Gly Gln Gly Asn Gly Gln Gly Arg Pro Ser His Ser Tyr Ser Ala
                20                  25                  30

Pro Gly Gln Gly Gln Gly Asn Gly Gln Gly Arg Pro Ser His Ser Tyr
            35                  40                  45

Ser Ala Pro Gly Gln Gly Gln Gly Asn Gly Gln Gly Arg Pro Ser His
        50                  55                  60

Ser Tyr Ser Ala Pro Gly Gln Gly Gln Gly Asn Gly Gln Gly Arg Pro
65                  70                  75                  80

Ser His Ser Tyr Ser Ala Pro Gly Gln Gly Gln Gly Asn Gly Gln Gly
                85                  90                  95

Arg Pro Ser His Ser Tyr Ser Ala Pro Gly Gln Gly Gln Gly Asn Gly
            100                 105                 110

Gln Gly Arg Pro Ser His Ser Tyr Ser Ala Pro Gly Gln Gly Gln Gly
        115                 120                 125

Asn Gly Gln Gly Arg Pro Ser His Ser Tyr Ser Ala Pro Gly Gln Gly
    130                 135                 140
```

Gln Gly Asn Gly Gln Gly Arg Pro Ser His Ser Tyr Ser Ala Pro Gly
145                 150                 155                 160

Gln Gly Gln Gly Asn Gly Gln Gly Arg Pro Ser His Ser Tyr Ser Ala
            165                 170                 175

Pro Gly Gln Gly Gln Gly Asn Gly Gln Gly Arg Pro Ser His Ser Tyr
        180                 185                 190

Ser Ala Pro Gly Gln Gly Gln Gly Asn Gly Gln Gly Arg Pro Ser His
    195                 200                 205

Ser Tyr Ser Ala Pro Gly Gln Gly Gln Gly Asn Gly Gln Gly Arg Pro
210                 215                 220

Ser His Ser Tyr Ser Ala Pro Gly Gln Gly Gln Gly Asn Gly Gln Gly
225                 230                 235                 240

Arg Pro Ser His Ser Tyr Ser Ala Pro Gly Gln Gly Gln Gly Asn Gly
                245                 250                 255

Gln Gly Arg Pro Ser His Ser Tyr Ser Ala Pro Gly Gln Gly Gln Gly
            260                 265                 270

Asn Gly Gln Gly Arg Pro Ser His Ser Tyr Ser Ala Pro Gly Gln Gly
        275                 280                 285

Gln Gly Asn Gly Gln Gly Arg Pro Ser His Ser Tyr Ser Ala Pro Gly
    290                 295                 300

Gln Gly Gln Gly Asn Gly Gln Gly Arg Pro Ser His Ser Tyr Ser Ala
305                 310                 315                 320

Pro Gly Gln Gly Gln Gly Asn Gly Gln Gly Arg Pro Ser His Ser Tyr
                325                 330                 335

Ser Ala Pro Gly Gln Gly Gln Gly Asn Gly Gln Gly Arg Pro Ser His
            340                 345                 350

Ser Tyr Ser Ala Pro Gly Gln Gly Gln Gly Asn Gly Gln Gly Arg Pro
        355                 360                 365

Ser His Ser Tyr Ser Ala Pro Gly Gln Gly Gln Gly Asn Leu Pro Asn
    370                 375                 380

Thr Gly Gly His His His His His
385                 390

<210> SEQ ID NO 4
<211> LENGTH: 404
<212> TYPE: PRT
<213> ORGANISM: Artificial Sequence
<220> FEATURE:
<223> OTHER INFORMATION: SEQ ID NO: 4 depicts the protein sequence of
      MODELAS1776

<400> SEQUENCE: 4

Met His His His His His Asp Asp Asp Lys Gly Gly Gly Gln
1               5                   10                  15

Gly Arg Pro Ser His Ser Tyr Ser Ala Pro Gly Gln Gly Gln Gly Asn
                20                  25                  30

Gly Gln Gly Arg Pro Ser His Ser Tyr Ser Ala Pro Gly Gln Gly Gln
            35                  40                  45

Gly Asn Gly Gln Gly Arg Pro Ser His Ser Tyr Ser Ala Pro Gly Gln
50                  55                  60

Gly Gln Gly Asn Gly Gln Gly Arg Pro Ser His Ser Tyr Ser Ala Pro
65                  70                  75                  80

Gly Gln Gly Gln Gly Asn Gly Gln Gly Arg Pro Ser His Ser Tyr Ser
                85                  90                  95

Ala Pro Gly Gln Gly Gln Gly Asn Gly Gln Gly Arg Pro Ser His Ser
            100                 105                 110

Tyr Ser Ala Pro Gly Gln Gln Gly Asn Gly Gln Gly Arg Pro Ser
            115                 120                 125

His Ser Tyr Ser Ala Pro Gly Gln Gln Gly Asn Gly Gln Gly Arg
    130                 135                 140

Pro Ser His Ser Tyr Ser Ala Pro Gly Gln Gln Gly Asn Gly Gln
145                 150                 155                 160

Gly Arg Pro Ser His Ser Tyr Ser Ala Pro Gly Gln Gln Gly Asn
                165                 170                 175

Gly Gln Gly Arg Pro Ser His Ser Tyr Ser Ala Pro Gly Gln Gln
            180                 185                 190

Gly Asn Gly Gln Gly Arg Pro Ser His Ser Tyr Ser Ala Pro Gly Gln
        195                 200                 205

Gly Gln Gly Asn Gly Gln Gly Arg Pro Ser His Ser Tyr Ser Ala Pro
    210                 215                 220

Gly Gln Gly Gln Gly Asn Gly Gln Gly Arg Pro Ser His Ser Tyr Ser
225                 230                 235                 240

Ala Pro Gly Gln Gly Gln Gly Asn Gly Gln Gly Arg Pro Ser His Ser
                245                 250                 255

Tyr Ser Ala Pro Gly Gln Gly Gln Gly Asn Gly Gln Gly Arg Pro Ser
            260                 265                 270

His Ser Tyr Ser Ala Pro Gly Gln Gln Gly Asn Gly Gln Gly Arg
    275                 280                 285

Pro Ser His Ser Tyr Ser Ala Pro Gly Gln Gln Gly Asn Gly Gln
290                 295                 300

Gly Arg Pro Ser His Ser Tyr Ser Ala Pro Gly Gln Gln Gly Asn
305                 310                 315                 320

Gly Gln Gly Arg Pro Ser His Ser Tyr Ser Ala Pro Gly Gln Gln
            325                 330                 335

Gly Asn Gly Gln Gly Arg Pro Ser His Ser Tyr Ser Ala Pro Gly Gln
        340                 345                 350

Gly Gln Gly Asn Gly Gln Gly Arg Pro Ser His Ser Tyr Ser Ala Pro
            355                 360                 365

Gly Gln Gly Gln Gly Asn Gly Gln Gly Arg Pro Ser His Ser Tyr Ser
    370                 375                 380

Ala Pro Gly Gln Gly Gln Gly Asn Leu Pro Asn Thr Gly Gly His His
385                 390                 395                 400

His His His His

<210> SEQ ID NO 5
<211> LENGTH: 512
<212> TYPE: PRT
<213> ORGANISM: Artificial Sequence
<220> FEATURE:
<223> OTHER INFORMATION: SEQ ID NO: 5 depicts the protein sequence of
      MODELAS1777

<400> SEQUENCE: 5

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

```
Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala His His His
            100                 105                 110

His His His Asp Asp Asp Lys Gly Gly Gln Gly Arg Pro Ser
        115                 120                 125

Asp Ser Tyr Gly Ala Pro Gly Gln Gly Gln Gly Asn Gly Gln Gly Arg
        130                 135                 140

Pro Ser Asp Ser Tyr Gly Ala Pro Gly Gln Gly Gln Gly Asn Gly Gln
145                 150                 155                 160

Gly Arg Pro Ser Asp Ser Tyr Gly Ala Pro Gly Gln Gly Gln Gly Asn
                165                 170                 175

Gly Gln Gly Arg Pro Ser Asp Ser Tyr Gly Ala Pro Gly Gln Gly Gln
            180                 185                 190

Gly Asn Gly Gln Gly Arg Pro Ser Asp Ser Tyr Gly Ala Pro Gly Gln
        195                 200                 205

Gly Gln Gly Asn Gly Gln Gly Arg Pro Ser Asp Ser Tyr Gly Ala Pro
210                 215                 220

Gly Gln Gly Gln Gly Asn Gly Gln Gly Arg Pro Ser Asp Ser Tyr Gly
225                 230                 235                 240

Ala Pro Gly Gln Gly Gln Gly Asn Gly Gln Gly Arg Pro Ser Asp Ser
                245                 250                 255

Tyr Gly Ala Pro Gly Gln Gly Gln Gly Asn Gly Gln Gly Arg Pro Ser
            260                 265                 270

Asp Ser Tyr Gly Ala Pro Gly Gln Gly Gln Gly Asn Gly Gln Gly Arg
        275                 280                 285

Pro Ser Asp Ser Tyr Gly Ala Pro Gly Gln Gly Gln Gly Asn Gly Gln
        290                 295                 300

Gly Arg Pro Ser Asp Ser Tyr Gly Ala Pro Gly Gln Gly Gln Gly Asn
305                 310                 315                 320

Gly Gln Gly Arg Pro Ser Asp Ser Tyr Gly Ala Pro Gly Gln Gly Gln
                325                 330                 335

Gly Asn Gly Gln Gly Arg Pro Ser Asp Ser Tyr Gly Ala Pro Gly Gln
            340                 345                 350

Gly Gln Gly Asn Gly Gln Gly Arg Pro Ser Asp Ser Tyr Gly Ala Pro
        355                 360                 365

Gly Gln Gly Gln Gly Asn Gly Gln Gly Arg Pro Ser Asp Ser Tyr Gly
        370                 375                 380

Ala Pro Gly Gln Gly Gln Gly Asn Gly Gln Gly Arg Pro Ser Asp Ser
385                 390                 395                 400

Tyr Gly Ala Pro Gly Gln Gly Gln Gly Asn Gly Gln Gly Arg Pro Ser
                405                 410                 415

Asp Ser Tyr Gly Ala Pro Gly Gln Gly Gln Gly Asn Gly Gln Gly Arg
            420                 425                 430

Pro Ser Asp Ser Tyr Gly Ala Pro Gly Gln Gly Gln Gly Asn Gly Gln
        435                 440                 445

Gly Arg Pro Ser Asp Ser Tyr Gly Ala Pro Gly Gln Gly Gln Gly Asn
        450                 455                 460

Gly Gln Gly Arg Pro Ser Asp Ser Tyr Gly Ala Pro Gly Gln Gly Gln
465                 470                 475                 480
```

Gly Asn Gly Gln Gly Arg Pro Ser Asp Ser Tyr Gly Ala Pro Gly Gln
            485                 490                 495

Gly Gln Gly Asn Leu Pro Asn Thr Gly Gly His His His His His His
        500                 505                 510

<210> SEQ ID NO 6
<211> LENGTH: 1182
<212> TYPE: DNA
<213> ORGANISM: Artificial Sequence
<220> FEATURE:
<223> OTHER INFORMATION: SEQ ID NO: 6 depicts the DNA sequence of
      MODELAS1775-v2

<400> SEQUENCE: 6

| | | | |
|---|---|---|---|
| atgggtggtg gtcaaggtcg tccatctcat tcttattctg ctccaggtca gggccaaggt | 60 |
| aacggtcaag tcgtccgtc tcactcttat tccgctccag gccaaggtca gggcaacggc | 120 |
| cagggtcgtc cttcccacag ctactctgca ccgggccagg tcaaggcaa cggtcaaggc | 180 |
| cgccttctc actcttattc tgctccgggc agggtcagg gtaacggtca gggtcgtcca | 240 |
| agccattctt attccgcccc gggtcaaggc cagggtaacg ccagggtcg cccgagccac | 300 |
| tcttactctg ctccgggcca aggccagggt aatggccaag tcgtccgtc ccactcttac | 360 |
| agcgctccag gccagggcca gggcaacggc cagggccgcc cgtcccactc ctactctgcg | 420 |
| ccaggtcaag tcagggcaa cggtcagggc cgtccttctc attcctactc cgctccgggt | 480 |
| caaggtcaag gtaatggtca gggtcgcccg tctcattcct acagcgctcc gggtcagggt | 540 |
| cagggcaatg ccaaggccg tccgtctcac tcctatagcg ctccaggtca aggtcaaggt | 600 |
| aatggtcaag tcgtccgtc tcatagctat agcgccccag gtcagggcca gggcaacggc | 660 |
| cagggtcgcc cgagccactc ctactctgcc ccaggtcaag tcagggcaa tggtcagggc | 720 |
| cgtcctagcc actcttactc cgcgccaggc cagggccaag gtaacggcca aggccgtccg | 780 |
| agccactctt attctgctcc gggccaaggt caaggtaatg ccaaggtcg cccttctcac | 840 |
| tcctattccg ctccgggcca gggccagggt aatggtcagg tcgcccgtc ccacagctat | 900 |
| tccgcaccgg gtcagggcca aggcaacggt caaggtcgtc cgtcccattc ttacagcgct | 960 |
| cctggtcagg gtcaaggcaa cggccaaggc cgccatctc acagctacag cgcgccaggt | 1020 |
| caaggccaag gcaatggcca gggccgcccg tcccactctt actctgcacc gggccagggt | 1080 |
| cagggtaatg ccagggtcg tccgagccat tcctattccg caccaggtca gggtcagggc | 1140 |
| aacctgccga cactggtgg tcaccaccac caccaccact ga | 1182 |

<210> SEQ ID NO 7
<211> LENGTH: 1214
<212> TYPE: DNA
<213> ORGANISM: Artificial Sequence
<220> FEATURE:
<223> OTHER INFORMATION: SEQ ID NO: 7 depicts the DNA sequence of
      MODELAS1776

<400> SEQUENCE: 7

| | | | |
|---|---|---|---|
| atgcatcacc atcatcatca cgacgacgac gacaagggtg gtggtcaagg tcgtccatct | 60 |
| cattcttatt ctgctccagg tcagggccaa ggtaacggtc aaggtcgtcc gtctcactct | 120 |
| tattccgctc caggccaagg tcagggcaac ggccagggtc gtccttccca gctactctct | 180 |
| gcaccgggcc aggtcaagg caacggtcaa ggccgcccct tcactcttta ttctgctccg | 240 |
| ggccagggtc aggtaacgg tcagggtcgt ccaagccatt cttattccgc cccgggtcaa | 300 |
| ggccagggta acggccaggg tcgcccgagc cactcttact ctgctccggg ccaaggccag | 360 |

```
ggtaatggcc aaggtcgtcc gtcccactct tacagcgctc caggccaggg ccagggcaac    420
ggccagggcc gcccgtccca ctcctactct gcgccaggtc aaggtcaggg caacggtcag    480
ggccgtcctt ctcattccta ctccgctccg ggtcaaggtc aaggtaatgg tcagggtcgc    540
ccgtctcatt cctacagcgc tccgggtcag ggtcagggca atggccaagg ccgtccgtct    600
cactcctata gcgctccagg tcaaggtcaa ggtaatggtc aaggtcgtcc gtctcatagc    660
tatagcgccc caggtcaggg ccagggcaac ggccagggtc gcccgagcca ctcctactct    720
gccccaggtc aaggtcaggg caatggtcag ggccgtccta gccactctta ctccgcgcca    780
ggccagggcc aaggtaacgg ccaaggccgt ccgagccact cttattctgc tccgggccaa    840
ggtcaaggta atggccaagg tcgcccttct cactcctatt ccgctccggg ccagggccag    900
ggtaatggtc agggtcgccc gtcccacagc tattccgcac cgggtcaggc caaggcaacg    960
gtcaaggtcg tccgtcccat tcttacagcg ctcctggtca gggtcaaggc aacggccaag   1020
gccgcccatc tcacagctac agcgcgccag gtcaaggcca aggcaatggc cagggccgcc   1080
cgtcccactc ttactctgca ccgggccagg gtcagggtaa tggccagggt cgtccgagcc   1140
attcctattc cgcaccaggt cagggtcagg gcaacctgcc gaacactggt ggtcaccacc   1200
accaccacca ctga                                                    1214

<210> SEQ ID NO 8
<211> LENGTH: 1539
<212> TYPE: DNA
<213> ORGANISM: Artificial Sequence
<220> FEATURE:
<223> OTHER INFORMATION: SEQ ID NO: 8 depicts the DNA sequence of
      MODELAS1777

<400> SEQUENCE: 8
atgagcgata aaattattca cctgactgac gacagttttg acacggatgt actcaaagcg     60
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggcccat caccatcatc atcacgacga cgacgacaag    360
ggtggtggtc aaggtcgtcc gtctgattct tatggtgctc ctggtcaagg tcaaggcaac    420
ggccaaggcc gtccgtctga ctcttatggc gccccaggcc aggtcaagg caatggtcag    480 ggtcgcccat ctgactccta tggcgcgcca gtcagggtc aaggtaacgg tcaaggccgt    540
ccttctgatt cctacggcgc acctggtcag ggccaaggta acggcaaggg tcgtccgagc    600
gactcttacg gtgccccggg tcaaggccag ggtaacggtc agggtcgtcc gtccgacagc    660
tatggtgcgc cgggccaggg ccagggcaat ggccagggcc gtccgagcga tagctatggt    720
gctccgggcc agggtcaggg taacggccag ggtcgcccgt ctgacagcta cggtgcgccg    780
ggtcagggtc agggcaacgg ccagggtcgt cctagcgaca gctacggtgc accgggtcaa    840
ggccaaggca acggtcaggg ccgtccatct gatagctacg gtgctccggg tcaaggtcaa    900
ggtaatggcc aaggtcgtcc atctgattct tatggtgctc ctggtcaggg tcaaggtaac    960
ggtcaaggcc gcccgtctga ctcctacggt gcgccgggtc agggtcaggg caacggccaa   1020
ggtcgcccgt ctgatagcta cggtgcacct ggtcaggtc agggtaacgg ccagggtcgc   1080
ccgagcgact cttatggcgc tccaggtcaa ggtcaaggca acggccaggg tcgtccatcc   1140
```

```
gatagctacg gcgcaccggg ccaaggccag ggcaacggtc agggtcgtcc gtctgattct    1200
tacggtgctc caggccaggg tcaaggcaat ggtcagggtc gcccatctga ttcctacggc    1260
gcgccgggcc aaggtcaggg taatggccag ggccgtccta gcgattccta cggtgctccg    1320
ggtcaaggtc aaggtaatgg tcagggccgt ccgtccgact cctacggtgc accgggtcag    1380
ggccaaggca acggtcaagg tcgtccaagc gactcttatg gcgcccagg tcaaggccag    1440 ggtaacggtc aaggccgtcc aagcgactcc tatggcgcac caggccaggg ccaaggtaac    1500
ctgccaaaca ccggtggcca ccaccaccac caccactga                           1539
```

MODULAR RESILIN-MIMETIC ELASTOMERIC PLATFORM

CROSS-REFERENCE TO RELATED APPLICATIONS

This application is a Section 371 of International Application No. PCT/IN2017/050538, filed Nov. 17, 2017, which was published in the English language on May 24, 2018 under International Publication No. WO 2018/092156 A1, and claims priority under 35 U.S.C. § 119(b) to Indian Application No. 201641017212, filed Nov. 18, 2016, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "689370_4US Sequence Listing," a creation date of May 10, 2019 and having a size of 18 KB. The sequence listing submitted via EFS-Web is part of the specification and is herein incorporated by reference in its entirety.

FIELD OF INVENTION

The present disclosure relates to the field of tuneable hydrogel designs comprising repeating units of bio-inspired peptide blocks for bio-medical applications.

BACKGROUND OF THE INVENTION

Molecular self-assembly has attracted growing international research efforts and interest due to its central importance in biology and its role in understanding of molecular origin of a wide range of diseases (Burkoth et al., 1998; Lashuel et al., 2000; Yamada et al., 1998). With the onset of world-wide activities in nano-scale science and nanotechnology, molecular self-assembly has also provided inspiration for innovation (Wilson et al., 2002) and new product development in the fields of nanostructured and biologically inspired materials, for example, drug delivery, wound healing and tissue engineering, and novel processing routes (Collier et al., 2001; de Loos, 2001; Gronwald et al., 2002; Hanabusa et al., 1996; Marini et al., 2002; Qu et al., 2000; Terech and Weiss, 1997).

Molecular self-assembly is an attractive route to nanostructured materials, which can have a number of key performance properties such as massive surface area and thus increased functional properties such as adsorption or binding. Furthermore, molecular self-assembly is a spontaneous phenomenon, that is, thermodynamically driven; one implication is that self-assembling nanostructures are self-healing; they further provide a cheap, easy, and potentially fast methodology for bulk production of complex functional structures. The simple processes involved in the production of self-assembling structures using conventional techniques under mild conditions, are particularly suited to large-scale industrial applications.

Bio-inspired, protein-like self-assembly is one of the most fascinating and fast-growing areas within the domain of molecular self-assembly. Proteins and peptides are the most versatile biological building blocks in nature in terms of chemistry, conformation, and functionality. They offer routes to sustainable, large-scale production since they can be produced not only by chemical means but also through genetic engineering. Another advantage is that they are environmentally friendly, "green" polymers. Also, through the control at the level of amino acids, which are the building blocks of a protein molecule, it is possible to achieve precise control of properties, such as intermolecular interactions, nanostructure, (bio-) activity and supra-molecular assembly. Unfortunately, a major drawback is that, the immense chemical and conformational complexities of macro-molecules make the above-mentioned phenomena difficult to understand; and thus, to predict and control accurately and reliably.

Elastomeric proteins occur in a wide range of biological systems, from plants and invertebrates to humans, where they have evolved to fulfill precise functional roles. The majority of these proteins possess rubber-like elasticity, undergoing high deformation without rupture and then returning to their original state on removal of the stress, with virtually all the energy stored on deformation being returned. The second stage of this process, i.e. the recoil, is passive and does not require an input of energy.

In order to achieve these properties, the chains of a protein elastomer must be flexible and rather free to respond rapidly to an applied force. Further, they must also form a network of monomers stabilized by cross-links between non-elastic domains. The elastic properties vary with the length of the flexible domain, the extent of cross-linking etc.

Elastomeric proteins are widely distributed in the animal kingdom, but only a small number have been characterized in detail. Their intrinsic insolubility and their non-globular nature have limited the means of direct analysis of structure-function, whereas sequence information from molecular-genetic studies has only become available in recent years.

The best-known protein elastomer is elastin. Elastin is widely distributed in vertebrate tissues and is responsible for elasticity of the aorta and skin of mammals. It performs various functions, acting statically in dermis to resist long-term forces and dynamically in arteries to store and release energy rapidly. It is also present in the ligamentum nuchae which is involved in raising the heads of grazing hoofed animals. Human life is majorly dependent on the elastic properties of elastin. Together with other structural proteins, elastin forms the fabric of extensible tissues, including skin, blood vessels and elastic ligaments, and provides the elasticity required for proper physiological function. Elastin is a major component of large arteries; bovine aorta is composed of nearly 50% elastin. The aorta expands when the heart contracts (during systole), and recoils elastically when the heart refills with blood (during diastole). In the walls of the aorta, elastin function in tandem with collagen to produce a "J-shaped" stress-strain curve. Elastin is responsible for the initial low stiffness region of the curve, while collagen confers increased stiffness at higher strains. Thus, collagen provides the strength required to prevent rupture due to high blood pressure, while the resilience and extensibility of the aorta imparted by elastin minimize the energetic demands on the heart and ensure smooth blood flow to tissues throughout the body. In addition to extensibility and resilience, elastin possesses remarkable durability: once laid down in tissue during development, elastin does not turn over at an appreciable rate. In order to sustain a lifetime of breaths and heartbeats, elastin must therefore undergo billions of stretching-relaxation cycles without damage or permanent deformation. Unlike elastin in blood vessels and lungs, elastin in the uterus is degraded and replaced during adulthood. In order to accommodate the rapid growth and motion of the fetus, the uterus requires significant extensibility. Accordingly, during pregnancy, uterine elastin content increases by more than 500%, the majority of which is quickly degraded post-partum. As a result of elastin's impressive diversity of biological roles and exceptional mechanical properties, it is the best-characterized rubber-like elastomeric protein. Elastin is secreted as a soluble precursor, tropoelastin, before forming the amorphous component of elastic fibers. Tropoelastin consists of alternating repetitive hydrophobic domains of variable length (predominantly consisting of proline, valine and glycine), and alanine-rich, lysine-containing domains that form crosslinks. Fibrillin, which forms the scaffold for elastin in vertebrate tissues, has also been shown to have elastic properties.

Resilin another elastomeric protein found exclusively in arthropods. It displays mechanical properties similar to elastin and it performs functions requiring high extensibility, high resilience, high fatigue life time, varied frequency response etc. For example, fleas use the elastic properties of resilin to jump 150 times their body length while accelerating 50 times faster than a space shuttle. Highly skilled and efficient fliers like dragonflies and mosquitoes owe much of their aerodynamic feats to resilin, which allows them to flap their wings for more than 500 million cycles during their lifetime. Resilin provides the elastic properties in the mechanism of Cicadas, which produces sharply resonant sound pulses at over 13 kHz. Resilin is also found at the base of sensory hairs, where its ability to retain its shape for long periods ensures that the hairs always return to the same position after moving, obviating the need for a 'null position' signal from the nervous system. Resilin has been reported in some cuticular structures which are stretchable, but do not possess long-range elasticity, such as the abdominal wall of physogastric termite queens and of some ants, where the volume of the abdomen in workers can be increased drastically for the storage of nectar.

Spider silk: Spiders produce silks with a variety (sometimes extreme) of mechanical properties. The dragline silks form the dropping line and web framework, and are stiffer than the flagelliform silks that form the spiral, capturing part of the web. Whereas, dragline silk, which possesses high tensile strength, extends by approximately 30%, the flagelliform silks extend by approx. 200% of their length without breaking. The flagelliform silks have similar properties to a slightly crosslinked rubber; that is, a combination of low stiffness and high extensibility. The combination of different silk proteins allows the spider to produce fibers with different mechanical properties and allows the web to absorb the energy of the impacting insect without catapulting the insect out of the web.

Collagen fibers of tendons are virtually inextensible; but, like steel wire, they also have elastic properties. This elasticity is exploited by animals during rapid running and, in doing so, their tendons act as energy stores for rebounds, thus providing more efficient running. Biologically active protein elastomers are unknown in plants, but the elastic properties of the gluten proteins of wheat grain have been well documented. Wheat gluten corresponds to the seed storage proteins that form an elastic network in dough. Although the sole function of gluten proteins is to store carbon and nitrogen, they have elastic properties, which are probably a fortuitous consequence of structures that have evolved to facilitate their efficient storage and packaging into protein bodies in the seed.

Most of these elastomeric proteins exist naturally in the form of macromolecular assemblies called hydrogels. Hydrogels are three-dimensional polymer networks capable of swelling in water or biological fluids, and retain a large amount of fluids in the swollen state. Their ability to absorb water is due to the presence of hydrophilic groups such as —OH, —CONH—, —CONH$_2$, —COOH and —SO$_3$H. Hydrogels have physical properties similar to that of living tissue, and the similarity is due to high water content, soft and rubber like consistency, and low interfacial tension with water or biological fluids. Hydrogels of biopolymers and their conjugates have emerged as an important class of soft condensed matter in recent years.

SUMMARY OF THE INVENTION

In an aspect of the present disclosure, there is provided a synthetic polypeptide comprising "n" number of repeats of a sequence as set forth in SEQ ID NO: 1 or SEQ ID NO: 2.

In an aspect of the present disclosure, there is provided a DNA construct comprising a polynucleotide fragment encoding a synthetic polypeptide comprising "n" number of repeats of a sequence as set forth in SEQ ID NO: 1 or SEQ ID NO: 2, operably linked to a promoter.

In an aspect of the present disclosure, there is provided a DNA vector comprising a DNA construct, said DNA construct comprising a polynucleotide fragment encoding a synthetic polypeptide comprising "n" number of repeats of a sequence as set forth in SEQ ID NO: 1 or SEQ ID NO: 2, operably linked to a promoter.

In an aspect of the present disclosure, there is provided a recombinant host cell comprising a DNA construct, said DNA construct comprising a polynucleotide fragment encoding a synthetic polypeptide comprising "n" number of repeats of a sequence as set forth in SEQ ID NO: 1 or SEQ ID NO: 2; or comprising a DNA vector, said DNA vector comprising said DNA construct, operably linked to a promoter.

In an aspect of the present disclosure, there is provided a method of obtaining a synthetic polypeptide comprising "n" number of repeats of a sequence as set forth in SEQ ID NO: 1 or SEQ ID NO: 2, said method comprising: (a) obtaining a recombinant host cell comprising: a DNA construct, said DNA construct comprising a polynucleotide fragment encoding a synthetic polypeptide comprising "n" number of repeats of a sequence as set forth in SEQ ID NO: 1 or SEQ ID NO: 2, operably linked to a promoter; or comprising a DNA vector, said DNA vector comprising said DNA construct; (b) culturing said recombinant host cell under conditions conducive for expression of said synthetic polypeptide; and (c) isolating and purifying said synthetic polypeptide.

In an aspect of the present disclosure, there is provided an elastomeric hydrogel comprising a synthetic polypeptide, said synthetic polypeptide comprising "n" number of repeats of a sequence as set forth in SEQ ID NO: 1 or SEQ ID NO: 2, covalently linked to at least one synthetic polypeptide.

In an aspect of the present disclosure, there is provided a method of obtaining elastomeric hydrogel comprising a synthetic polypeptide, said synthetic polypeptide comprising "n" number of repeats of a sequence as set forth in SEQ ID NO: 1 or SEQ ID NO: 2.

In an aspect of the present disclosure, there is provided a synthetic polypeptide comprising "n" number of repeats of a sequence as set forth in SEQ ID NO: 1 or SEQ ID NO: 2, for use in preparing elastomeric hydrogels.

In an aspect of the present disclosure, there is provided an elastomeric hydrogel comprising a synthetic polypeptide, said synthetic polypeptide comprising "n" number of repeats of a sequence as set forth in SEQ ID NO: 1 or SEQ ID NO: 2, for use in bio-medical applications.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF THE ACCOMPANYING DRAWINGS

The patent or application file contains at least one drawing executed in color. Copies of the patent or patent application publication with color drawing(s) will be provided by the Office upon request and payment of the necessary fee.

The following drawings form part of the present specification and are included to further illustrate aspects of the present disclosure. The disclosure may be better understood by reference to the drawings in combination with the detailed description of the specific embodiments presented herein.

Figure 5A:
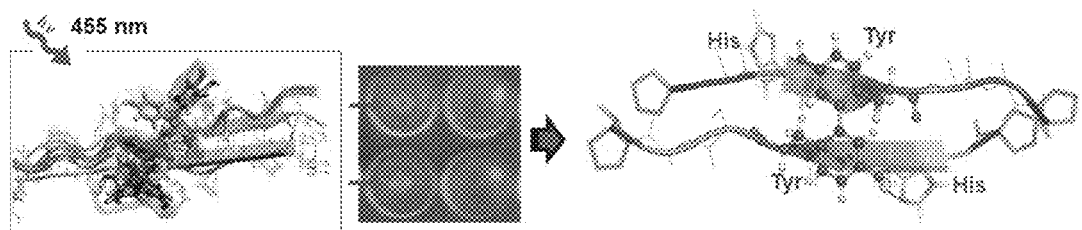
Figure 5B:
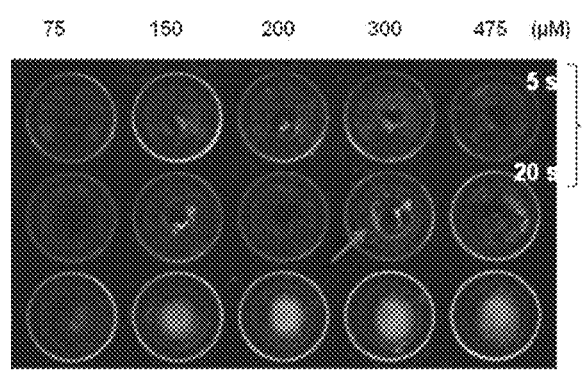
Figure 5C:
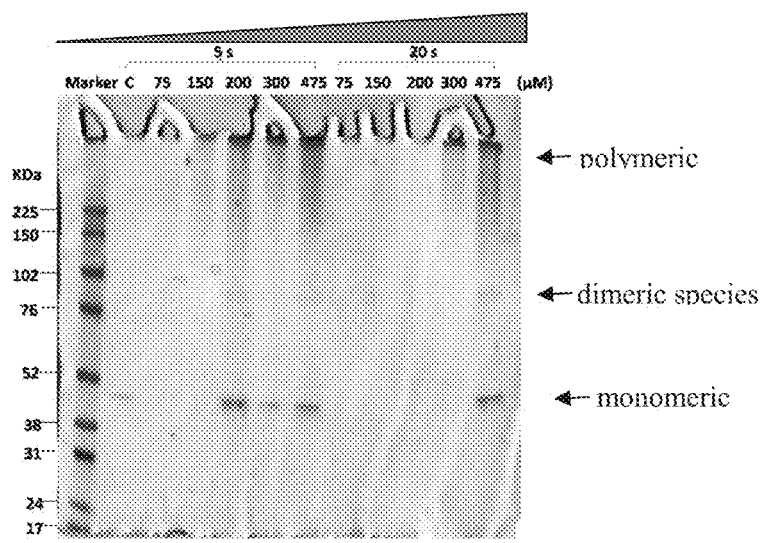

FIG. 5A depicts the secondary structure formation as a result of photo cross-linking of polymer 1775-v2 (SEQ ID NO: 3) in presence of light at 455 nm; FIG. 5B depicts hydrogel comprising polymer 1775-v2 (SEQ ID NO: 3) after photo-irradiation at 455 nm (pH 7.4); FIG. 5C depicts SDS PAGE gel of the photo-irradiated hydrogel of polymer 1775-v2 (SEQ ID NO: 3), in accordance with an embodiment of the present disclosure.

Figure 6A:
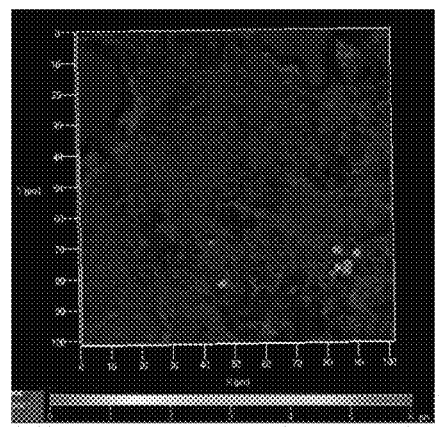
Figure 6B:
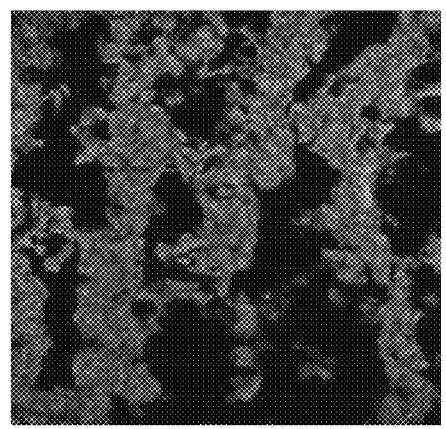

FIG. 6A depicts the confocal image showing polymer 1775-v2 (SEQ ID NO: 3) with encapsulated Sphero beads; FIG. 6B depicts confocal image of the polymer with encapsulated Alexa Fluor 488 nm, in accordance with an embodiment of the present disclosure.

Figure 7A:
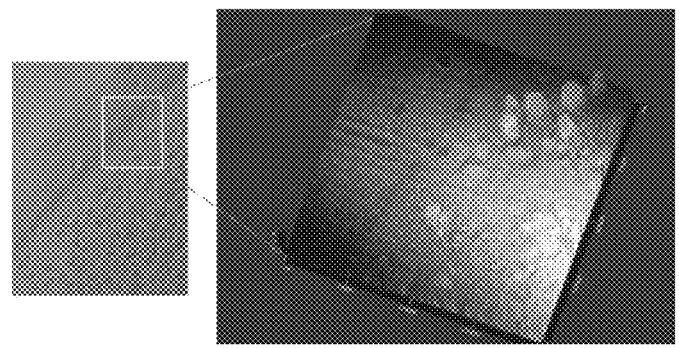
Figure 7B:
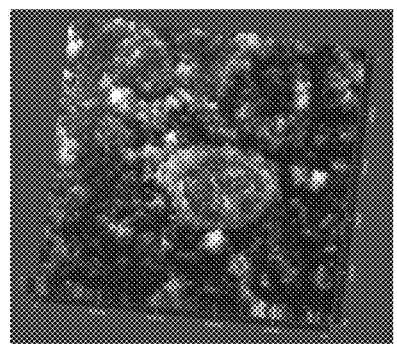

FIG. 7A depicts an intact hydrogel (polymer 1775-v2) boundary two days post swelling in DMEM/PBS without any of the encapsulated cells being released from the matrix due to degradation; FIG. 7B depicts the differential staining of nucleus (DAPI), cytoplasm (green), in accordance with an embodiment of the present disclosure.

DETAILED DESCRIPTION OF THE INVENTION

```
                             Sequences

SEQ ID NO: 1 depicts the peptide repeat sequence
PSHSYSAPGQGQGNGQG

SEQ ID NO: 2 depicts the peptide repeat sequence
PSDSYGAPGQGQGNGQG

SEQ ID NO: 3 depicts the protein sequence of MODELAS1775-v2
MGGGQGRPSHSYSAPGQGQGNGQGRPSHSYSAPGQGQGNGQGRPSHSYSAPGQGQGNGQ
GRPSHSYSAPGQGQGNGQGRPSHSYSAPGQGQGNGQGRPSHSYSAPGQGQGNGQGRPSHS
YSAPGQGQGNGQGRPSHSYSAPGQGQGNGQGRPSHSYSAPGQGQGNGQGRPSHSYSAPGQ
GQGNGQGRPSHSYSAPGQGQGNGQGRPSHSYSAPGQGQGNGQGRPSHSYSAPGQGQGNG
QGRPSHSYSAPGQGQGNGQGRPSHSYSAPGQGQGNGQGRPSHSYSAPGQGQGNGQGRPSH
SYSAPGQGQGNGQGRPSHSYSAPGQGQGNGQGRPSHSYSAPGQGQGNGQGRPSHSYSAPG
QGQGNGQGRPSHSYSAPGQGQGNLPNTGGHHHHHH SEQ ID NO: 4 depicts the protein sequence of MODELAS1776
MHHHHHHDDDDKGGGQGRPSHSYSAPGQGQGNGQGRPSHSYSAPGQGQGNGQGRPSHS
YSAPGQGQGNGQGRPSHSYSAPGQGQGNGQGRPSHSYSAPGQGQGNGQGRPSHSYSAPGQ
GQGNGQGRPSHSYSAPGQGQGNGQGRPSHSYSAPGQGQGNGQGRPSHSYSAPGQGQGNG
QGRPSHSYSAPGQGQGNGQGRPSHSYSAPGQGQGNGQGRPSHSYSAPGQGQGNGQGRPSH
SYSAPGQGQGNGQGRPSHSYSAPGQGQGNGQGRPSHSYSAPGQGQGNGQGRPSHSYSAPG
QGQGNGQGRPSHSYSAPGQGQGNGQGRPSHSYSAPGQGQGNGQGRPSHSYSAPGQGQGN
GQGRPSHSYSAPGQGQGNGQGRPSHSYSAPGQGQGNLPNTGGHHHHHH SEQ ID NO: 5 depicts the protein sequence of MODELAS1777
MSDKIIHLTDDSFDTDVLKADGAILVDFWAEWCGPCKMIAPILDEIADEYQGKLTVAKLNI
DQNPGTAPKYGIRGIPTLLLFKNGEVAATKVGALSKGQLKEFLDANLAHHHHHHDDDDKG
GGQGRPSDSYGAPGQGQGNGQGRPSDSYGAPGQGQGNGQGRPSDSYGAPGQGQGNGQG
RPSDSYGAPGQGQGNGQGRPSDSYGAPGQGQGNGQGRPSDSYGAPGQGQGNGQGRPSDS
YGAPGQGQGNGQGRPSDSYGAPGQGQGNGQGRPSDSYGAPGQGQGNGQGRPSDSYGAPG
QGQGNGQGRPSDSYGAPGQGQGNGQGRPSDSYGAPGQGQGNGQGRPSDSYGAPGQGQG
NGQGRPSDSYGAPGQGQGNGQGRPSDSYGAPGQGQGNGQGRPSDSYGAPGQGQGNGQG
RPSDSYGAPGQGQGNGQGRPSDSYGAPGQGQGNGQGRPSDSYGAPGQGQGNGQGRPSDS
YGAPGQGQGNGQGRPSDSYGAPGQGQGNLPNTGGHHHHHH SEQ ID NO: 6 depicts the DNA sequence of MODELAS1775-v2
ATGGGTGGTGGTCAAGGTCGTCCATCTCATTCTTATTCTGCTCCAGGTCAGGGCCAAGG
TAACGGTCAAGGTCGTCCGTC
TCACTCTTATTCCGCTCCAGGCCAAGGTCAGGGCAACGGCCAGGGTCGTCCTTCCCACA
GCTACTCTGCACCGGGCCAGGGTCAAGGCAACGGTCAAGGCCGCCCTTCTCACTCTTAT
TCTGCTCCGGGCCAGGGTCAGGGTAACGGTCAGGGTCGTCCAAGCCATTCTTATTCCGC
CCCGGGTCAAGGCCAGGGTAACGGCCAGGGTCGCCCGAGCCACTCTTACTCTGCTCCG
GGCCAAGGCCAGGGTAATGGCCAAGGTCGTCCGTCCCACTCTTACAGCGCTCCAGGCC
AGGGCCAGGGCAACGGCCAGGGCCGCCCGTCCCACTCCTACTCTGCGCCAGGTCAAGG
```

```
                                Sequences

TCAGGGCAACGGTCAGGGCCGTCCTTCTCATTCCTACTCCGCTCCGGGTCAAGGTCAAG
GTAATGGTCAGGGTCGCCCGTCTCATTCCTACAGCGCTCCGGGTCAGGGTCAGGGCAAT
GGCCAAGGCCGTCCGTCTCACTCCTATAGCGCTCCAGGTCAAGGTCAAGGTAATGGTCA
AGGTCGTCCGTCTCATAGCTATAGCGCCCCAGGTCAGGGCCAGGGCAACGGCCAGGGT
CGCCCGAGCCACTCCTACTCTGCCCCAGGTCAAGGTCAGGGCAATGGTCAGGGCCGTCC
TAGCCACTCTTACTCCGCGCCAGGCCAGGGCCAAGGTAACGGCCAAGGCCGTCCGAGC
CACTCTTATTCTGCTCCGGGCCAAGGTCAAGGTAATGGCCAAGGTCGCCCTTCTCACTC
CTATTCCGCTCCGGGCCAGGGCCAGGGTAATGGTCAGGGTCGCCCGTCCCACAGCTATT
CCGCACCGGGTCAGGGCCAAGGCAACGGTCAAGGTCGTCCGTCCCATTCTTACAGCGCT
CCTGGTCAGGGTCAAGGCAACGGCCAAGGCCGCCCATCTCACAGCTACAGCGCGCCAG
GTCAAGGCCAAGGCAATGGCCAGGGCCGCCCGTCCCACTCTTACTCTGCACCGGGCCA
GGGTCAGGGTAATGGCCAGGGTCGTCCGAGCCATTCCTATTCCGCACCAGGTCAGGGTC
AGGGCAACCTGCCGAACACTGGTGGTCACCACCACCACCACTGA

SEQ ID NO: 7 depicts the DNA sequence of MODELAS1776
ATGCATCACCATCATCATCACGACGACGACGACAAGGGTGGTGGTCAAGGTCGTCCAT
CTCATTCTTATTCTGCTCCAGGTCAGGGCCAAGGTAACGGTCAAGGTCGTCCGTCTCAC
TCTTATTCCGCTCCAGGCCAAGGTCAGGGCAACGGCCAGGGTCGTCCTTCCCACAGCTA
CTCTGCACCGGGCCAGGGTCAAGGCAACGGTCAAGGCCGCCCTTCTCACTCTTATTCTG
CTCCGGGCCAGGGTCAGGGTAACGGTCAGGGTCGTCCAAGCCATTCTTATTCCGCCCCG
GGTCAAGGCCAGGGTAACGGCCAGGGTCGCCCGAGCCACTCTTACTCTGCTCCGGGCC
AAGGCCAGGGTAATGGCCAAGGTCGTCCGTCCCACTCTTACAGCGCTCCAGGCCAGGG
CCAGGGCAACGGCCAGGGCCGCCCGTCCCACTCCTACTCTGCGCCAGGTCAAGGTCAG
GGCAACGGTCAGGGCCGTCCTTCTCATTCCTACTCCGCTCCGGGTCAAGGTCAAGGTAA
TGGTCAGGGTCGCCCGTCTCATTCCTACAGCGCTCCGGGTCAGGGTCAGGGCAATGGCC
AAGGCCGTCCGTCTCACTCCTATAGCGCTCCAGGTCAAGGTCAAGGTAATGGTCAAGGT
CGTCCGTCTCATAGCTATAGCGCCCCAGGTCAGGGCCAGGGCAACGGCCAGGGTCGCC
CGAGCCACTCCTACTCTGCCCCAGGTCAAGGTCAGGGCAATGGTCAGGGCCGTCCTAGC
CACTCTTACTCCGCGCCAGGCCAGGGCCAAGGTAACGGCCAAGGCCGTCCGAGCCACT
CTTATTCTGCTCCGGGCCAAGGTCAAGGTAATGGCCAAGGTCGCCCTTCTCACTCCTAT
TCCGCTCCGGGCCAGGGCCAGGGTAATGGTCAGGGTCGCCCGTCCCACAGCTATTCCGC
ACCGGGTCAGGGCCAAGGCAACGGTCAAGGTCGTCCGTCCCATTCTTACAGCGCTCCTGG
TCAGGGTCAAGGCAACGGCCAAGGCCGCCCATCTCACAGCTACAGCGCGCCAGGTCAA
GGCCAAGGCAATGGCCAGGGCCGCCCGTCCCACTCTTACTCTGCACCGGGCCAGGGTC
AGGGTAATGGCCAGGGTCGTCCGAGCCATTCCTATTCCGCACCAGGTCAGGGTCAGGG
CAACCTGCCGAACACTGGTGGTCACCACCACCACCACTGA SEQ ID NO: 8 depicts the DNA sequence of MODELAS1777
ATGAGCGATAAAATTATTCACCTGACTGACGACAGTTTTGACACGGATGTACTCAAAGC
GGACGGGGCGATCCTCGTCGATTTCTGGGCAGAGTGGTGCGGTCCGTGCAAAATGATC
GCCCCGATTCTGGATGAAATCGCTGACGAATATCAGGGCAAACTGACCGTTGCAAAAC
TGAACATCGATCAAAACCCTGGCACTGCGCCGAAATATGGCATCCGTGGTATCCCGACT
CTGCTGCTGTTCAAAAACGGTGAAGTGGCGGCAACCAAAGTGGGTGCACTGTCTAAAG
GTCAGTTGAAAGAGTTCCTCGACGCTAACCTGGCCCATCACCATCATCATCACGACGAC
GACGACAAGGGTGGTGGTCAAGGTCGTCCGTCTGATTCTTATGGTGGTCCTGGTCAAGG
TCAAGGCAACGGCCAAGGCCGTCCGTCTGACTCTTATGGCGCCCCAGGCCAGGGTCAA
GGCAATGGTCAGGGTCGCCCATCTGACTCCTATGGCGCGCCAGGTCAGGGTCAAGGTA
ACGGTCAAGGCCGTCCTTCTGATTCCTACGGCGCACCTGGTCAGGGCCAAGGTAACGGC
CAAGGTCGTCCGAGCGACTCTTACGGTGCCCCGGGTCAAGGCCAGGGTAACGGTCAGG
GTCGTCCGTCCGACAGCTATGGTGCGCCGGGCCAGGGCCAGGGCAATGGCCAGGGCCG
TCCGAGCGATAGCTATGGTGCTCCGGGCCAGGGTCAGGGTAACGGCCAGGGTCGCCCG
TCTGACAGCTACGGTGCGCGGGTCAGGGTCAGGGCAACGGCCAGGGTCGTCCTAGCG
ACAGCTACGGTGCACCGGGTCAAGGCCAAGGCAACGGTCAGGGCCGTCCATCTGATAG
CTACGGTGCTCCGGGTCAAGGTCAAGGTAATGGCCAAGGTCGTCCATCTGATTCTTATG
GTGCTCCTGGTCAGGGTCAAGGTAACGGTCAAGGCCGCCCGTCTGACTCCTACGGTGCG
CCGGGTCAGGGTCAGGGCAACGGCCAAGGTCGCCCGTCTGATAGCTACGGTGCACCTG
GTCAGGGTCAGGGTAACGGCCAGGGTCGCCCGAGCGACTCTTATGGCGCTCCAGGTCA
AGGTCAAGGCAACGGCCAGGGTCGTCCATCCGATAGCTACGGCGCACCGGGCCAAGGC
CAGGGCAACGGTCAGGGTCGTCCGTCTGATTCTTACGGTGCTCCAGGCCAGGGTCAAG
GCAATGGTCAGGGTCGCCCATCTGATTCCTACGGCGCGCCGGGCCAAGGTCAGGGTAA
TGGCCAGGGCCGTCCTAGCGATTCCTACGGTGCTCCGGGTCAAGGTCAAGGTAATGGTC
AGGGCCGTCCGTCCGACTCCTACGGTGCACCGGGTCAGGGCCAAGGCAACGGTCAAGG
TCGTCCAAGCGACTCTTATGGCGCCCCAGGTCAAGGCCAGGGTAACGGTCAAGGCCGT
CCAAGCGACTCCTATGGCGCACCAGGCCAGGGCCAAGGTAACCTGCCAAACACCGGTG
GCCACCACCACCACCACTGA
```

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

The term "peptide" may be interchangeably substituted with the term "polypeptide".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally-equivalent products, compositions, and methods are clearly within the scope of the disclosure, as described herein.

The present disclosure relates focuses to develop a biomaterial—amphiphilic hydrogel matrix for sustained release of various classes of drugs at different wound sites or other required places. The elastomer as disclosed herein is a hydrogel scaffold material that mimics extracellular matrix, and has capacity to load macromolecules, such as antibody and growth factors.

The present document discloses polypeptides for formation of different polymers. The document discloses two peptide repeat sequences represented by SEQ ID NO: 1 and SEQ ID NO: 2. Also, disclosed are the protein sequences formed by multiple repeat units of the above-mentioned repeat sequences. SEQ ID NO: 3 (MODELAS1775-v2) and SEQ ID NO: 4 (MODELAS1776) are protein sequences comprising multiple repeat units of peptide repeat—SEQ ID NO: 1. Whereas, SEQ ID NO: 5 (MODELAS1777) depict protein sequence comprising multiple repeat units of peptide repeat—SEQ ID NO: 2. The document also discloses methods for protein production, and methods for hydrogel formation using the polymer.

In an embodiment of the present disclosure, there is provided a synthetic polypeptide comprising "n" number of repeats of a sequence as set forth in SEQ ID NO: 1.

In an embodiment of the present disclosure, there is provided a synthetic polypeptide comprising "n" number of repeats of a sequence as set forth in SEQ ID NO: 2.

In an embodiment of the present disclosure, there is provided a synthetic polypeptide of sequence as set forth in SEQ ID NO: 3.

In an embodiment of the present disclosure, there is provided a synthetic polypeptide of sequence as set forth in SEQ ID NO: 4.

In an embodiment of the present disclosure, there is provided a synthetic polypeptide of sequence as set forth in SEQ ID NO: 5.

In an embodiment of the present disclosure, there is provided a synthetic polypeptide comprising "n" number of repeats of a sequence as set forth in SEQ ID NO: 1, said polypeptide having sequence as set forth in SEQ ID NO: 3.

In an embodiment of the present disclosure, there is provided a synthetic polypeptide comprising "n" number of repeats of a sequence as set forth in SEQ ID NO: 1, said polypeptide having sequence as set forth in SEQ ID NO: 4.

In an embodiment of the present disclosure, there is provided a synthetic polypeptide comprising "n" number of repeats of a sequence as set forth in SEQ ID NO: 2, said polypeptide having sequence as set forth in SEQ ID NO: 5.

In an embodiment of the present disclosure, there is provided a synthetic polypeptide encoded by a polynucleotide sequence as set forth in SEQ ID NO: 6.

In an embodiment of the present disclosure, there is provided a synthetic polypeptide encoded by a polynucleotide sequence as set forth in SEQ ID NO: 7.

In an embodiment of the present disclosure, there is provided a synthetic polypeptide encoded by a polynucleotide sequence as set forth in SEQ ID NO: 8.

In an embodiment of the present disclosure, there is provided a synthetic polypeptide comprising "n" number of repeats of a sequence as set forth in SEQ ID NO: 1, said polypeptide is encoded by a polynucleotide sequence as set forth in SEQ ID NO: 6.

In an embodiment of the present disclosure, there is provided a synthetic polypeptide comprising "n" number of repeats of a sequence as set forth in SEQ ID NO: 1, said polypeptide is encoded by a polynucleotide sequence as set forth in SEQ ID NO: 7.

In an embodiment of the present disclosure, there is provided a synthetic polypeptide comprising "n" number of repeats of a sequence as set forth in SEQ ID NO: 2, said polypeptide is encoded by a polynucleotide sequence as set forth in SEQ ID NO: 8.

In an embodiment of the present disclosure, there is provided a synthetic polypeptide of sequence as set forth in SEQ ID NO: 3, encoded by a polynucleotide fragment of sequence as set forth in SEQ ID NO: 6.

In an embodiment of the present disclosure, there is provided a synthetic polypeptide of sequence as set forth in SEQ ID NO: 4, encoded by a polynucleotide fragment of sequence as set forth in SEQ ID NO: 7.

In an embodiment of the present disclosure, there is provided a synthetic polypeptide of sequence as set forth in SEQ ID NO: 5, encoded by a polynucleotide fragment of sequence as set forth in SEQ ID NO: 8.

In an embodiment of the present disclosure, there is provided a DNA construct comprising a polynucleotide fragment encoding a synthetic polypeptide comprising "n" number of repeats of a sequence as set forth in SEQ ID NO: 1, operably linked to a promoter.

In an embodiment of the present disclosure, there is provided a DNA construct comprising a polynucleotide fragment encoding a synthetic polypeptide comprising "n" number of repeats of a sequence as set forth in SEQ ID NO: 2, operably linked to a promoter.

In an embodiment of the present disclosure, there is provided a DNA construct comprising a polynucleotide fragment encoding a synthetic polypeptide sequence as set forth in SEQ ID NO: 3, operably linked to a promoter.

In an embodiment of the present disclosure, there is provided a DNA construct comprising a polynucleotide fragment encoding a synthetic polypeptide sequence as set forth in SEQ ID NO: 4, operably linked to a promoter.

In an embodiment of the present disclosure, there is provided a DNA construct comprising a polynucleotide fragment encoding a synthetic polypeptide sequence as set forth in SEQ ID NO: 5, operably linked to a promoter.

In an embodiment of the present disclosure, there is provided a DNA construct comprising a polynucleotide fragment having sequence as set forth in SEQ ID NO: 6, operably linked to a promoter.

In an embodiment of the present disclosure, there is provided a DNA construct comprising a polynucleotide fragment having sequence as set forth in SEQ ID NO: 7, operably linked to a promoter.

In an embodiment of the present disclosure, there is provided a DNA construct comprising a polynucleotide fragment having sequence as set forth in SEQ ID NO: 8, operably linked to a promoter.

In an embodiment of the present disclosure, there is provided a DNA construct comprising a polynucleotide fragment having sequence as set forth in SEQ ID NO: 6, operably linked to promoter, said polynucleotide fragment encoding a polypeptide having sequence as set forth in SEQ ID NO: 3.

In an embodiment of the present disclosure, there is provided a DNA construct comprising a polynucleotide fragment having sequence as set forth in SEQ ID NO: 7, operably linked to promoter, said polynucleotide fragment encoding a polypeptide having sequence as set forth in SEQ ID NO: 4.

In an embodiment of the present disclosure, there is provided a DNA construct comprising a polynucleotide fragment having sequence as set forth in SEQ ID NO: 8, operably linked to promoter, said polynucleotide fragment encoding a polypeptide having sequence as set forth in SEQ ID NO: 5.

In an embodiment of the present disclosure, there is provided a DNA vector comprising a DNA construct, said DNA construct comprising a polynucleotide fragment encoding a synthetic polypeptide comprising "n" number of repeats of a sequence as set forth in SEQ ID NO: 1, operably linked to a promoter.

In an embodiment of the present disclosure, there is provided a DNA vector comprising a DNA construct, said DNA construct comprising a polynucleotide fragment encoding a synthetic polypeptide comprising "n" number of repeats of a sequence as set forth in SEQ ID NO: 2, operably linked to a promoter.

In an embodiment of the present disclosure, there is provided a DNA vector comprising a DNA construct, said DNA construct comprising a polynucleotide fragment encoding a synthetic polypeptide of sequence as set forth in SEQ ID NO: 3, operably linked to a promoter.

In an embodiment of the present disclosure, there is provided a DNA vector comprising a DNA construct, said DNA construct comprising a polynucleotide fragment encoding a synthetic polypeptide of sequence as set forth in SEQ ID NO: 4, operably linked to a promoter In an embodiment of the present disclosure, there is provided a DNA vector comprising a DNA construct, said DNA construct comprising a polynucleotide fragment encoding a synthetic polypeptide of sequence as set forth in SEQ ID NO: 5, operably linked to a promoter.

In an embodiment of the present disclosure, there is provided a DNA vector comprising a DNA construct, said DNA construct comprising a polynucleotide fragment having sequence as set forth in SEQ ID NO: 6, operably linked to a promoter.

In an embodiment of the present disclosure, there is provided a DNA vector comprising a DNA construct, said DNA construct comprising a polynucleotide fragment having sequence as set forth in SEQ ID NO: 7, operably linked to a promoter.

In an embodiment of the present disclosure, there is provided a DNA vector comprising a DNA construct, said DNA construct comprising a polynucleotide fragment having sequence as set forth in SEQ ID NO: 8, operably linked to a promoter.

In an embodiment of the present disclosure, there is provided a DNA vector comprising a DNA construct, said DNA construct comprising a polynucleotide fragment encoding a synthetic polypeptide of sequence as set forth in SEQ ID NO: 3, operably linked to a promoter, said polynucleotide fragment sequence is as set forth in SEQ ID NO: 6.

In an embodiment of the present disclosure, there is provided a DNA vector comprising a DNA construct, said DNA construct comprising a polynucleotide fragment encoding a synthetic polypeptide of sequence as set forth in SEQ ID NO: 4, operably linked to a promoter, said polynucleotide fragment sequence is as set forth in SEQ ID NO: 7.

In an embodiment of the present disclosure, there is provided a DNA vector comprising a DNA construct, said DNA construct comprising a polynucleotide fragment encoding a synthetic polypeptide of sequence as set forth in SEQ ID NO: 5, operably linked to a promoter, said polynucleotide fragment sequence is as set forth in SEQ ID NO: 8.

In an embodiment of the present disclosure, there is provided a recombinant host cell comprising a DNA construct, said DNA construct comprising a polynucleotide fragment encoding a synthetic polypeptide comprising "n" number of repeats of a sequence as set forth in SEQ ID NO: 1, operably linked to a promoter.

In an embodiment of the present disclosure, there is provided a recombinant host cell comprising a DNA construct, said DNA construct comprising a polynucleotide fragment encoding a synthetic polypeptide comprising "n" number of repeats of a sequence as set forth in SEQ ID NO: 2, operably linked to a promoter.

In an embodiment of the present disclosure, there is provided a recombinant host cell comprising a DNA construct, said DNA construct comprising a polynucleotide fragment encoding a synthetic polypeptide having sequence as set forth in SEQ ID NO: 3, operably linked to a promoter.

In an embodiment of the present disclosure, there is provided a recombinant host cell comprising a DNA construct, said DNA construct comprising a polynucleotide fragment encoding a synthetic polypeptide having sequence as set forth in SEQ ID NO: 4, operably linked to a promoter.

In an embodiment of the present disclosure, there is provided a recombinant host cell comprising a DNA construct, said DNA construct comprising a polynucleotide fragment encoding a synthetic polypeptide having sequence as set forth in SEQ ID NO: 5, operably linked to a promoter.

In an embodiment of the present disclosure, there is provided a recombinant host cell comprising a DNA construct, said DNA construct comprising a polynucleotide fragment having sequence as set forth in SEQ ID NO: 6, operably linked to a promoter.

In an embodiment of the present disclosure, there is provided a recombinant host cell comprising a DNA construct, said DNA construct comprising a polynucleotide fragment having sequence as set forth in SEQ ID NO: 7, operably linked to a promoter.

In an embodiment of the present disclosure, there is provided a recombinant host cell comprising a DNA construct, said DNA construct comprising a polynucleotide fragment having sequence as set forth in SEQ ID NO: 8, operably linked to a promoter.

In an embodiment of the present disclosure, there is provided a recombinant host cell comprising a DNA construct, said DNA construct comprising a polynucleotide fragment encoding a synthetic polypeptide having sequence as set forth in SEQ ID NO: 3, operably linked to a promoter, said polynucleotide fragment is as set forth in SEQ ID NO: 6.

In an embodiment of the present disclosure, there is provided a recombinant host cell comprising a DNA construct, said DNA construct comprising a polynucleotide fragment encoding a synthetic polypeptide having sequence as set forth in SEQ ID NO: 4, operably linked to a promoter, said polynucleotide fragment is as set forth in SEQ ID NO: 7.

In an embodiment of the present disclosure, there is provided a recombinant host cell comprising a DNA construct, said DNA construct comprising a polynucleotide fragment encoding a synthetic polypeptide having sequence as set forth in SEQ ID NO: 5, operably linked to a promoter, said polynucleotide fragment is as set forth in SEQ ID NO: 8.

In an embodiment of the present disclosure, there is provided a recombinant host cell comprising a DNA construct as described herein, wherein said recombinant host cell is of bacterial origin.

In an embodiment of the present disclosure, there is provided a recombinant host cell comprising a DNA construct as described herein, wherein said recombinant host cell is E. coli.

In an embodiment of the present disclosure, there is provided a recombinant host cell comprising a DNA construct as described herein, wherein said recombinant host cell is of fungal origin.

In an embodiment of the present disclosure, there is provided a recombinant host cell comprising a DNA construct as described herein, wherein said recombinant host cell is of plant origin.

In an embodiment of the present disclosure, there is provided a recombinant host cell comprising a DNA construct as described herein, wherein said recombinant host cell is of insect origin.

In an embodiment of the present disclosure, there is provided a recombinant host cell comprising a DNA construct as described herein, wherein said DNA construct is encoded in host cell genome.

In an embodiment of the present disclosure, there is provided a recombinant host cell comprising a DNA construct as described herein, wherein said DNA construct is encoded by extra-nuclear host cell genome.

In an embodiment of the present disclosure, there is provided a recombinant host cell comprising a DNA vector, said DNA vector comprising a DNA construct, said DNA construct comprising a polynucleotide fragment encoding a synthetic polypeptide comprising "n" number of repeats of a sequence as set forth in SEQ ID NO: 1, operably linked to a promoter.

In an embodiment of the present disclosure, there is provided a recombinant host cell comprising a DNA vector, said DNA vector comprising a DNA construct, said DNA construct comprising a polynucleotide fragment encoding a synthetic polypeptide comprising "n" number of repeats of a sequence as set forth in SEQ ID NO: 2, operably linked to a promoter.

In an embodiment of the present disclosure, there is provided a recombinant host cell comprising a DNA vector, said DNA vector comprising a DNA construct, said DNA construct comprising a polynucleotide fragment encoding a synthetic polypeptide having sequence as set forth in SEQ ID NO: 3, operably linked to a promoter.

In an embodiment of the present disclosure, there is provided a recombinant host cell comprising a DNA vector, said DNA vector comprising a DNA construct, said DNA construct comprising a polynucleotide fragment encoding a synthetic polypeptide having sequence as set forth in SEQ ID NO: 4, operably linked to a promoter.

In an embodiment of the present disclosure, there is provided a recombinant host cell comprising a DNA vector, said DNA vector comprising a DNA construct, said DNA construct comprising a polynucleotide fragment encoding a synthetic polypeptide having sequence as set forth in SEQ ID NO: 5, operably linked to a promoter.

In an embodiment of the present disclosure, there is provided a recombinant host cell comprising a DNA vector, said DNA vector comprising a DNA construct, said DNA construct comprising a polynucleotide fragment having sequence as set forth in SEQ ID NO: 6, operably linked to a promoter.

In an embodiment of the present disclosure, there is provided a recombinant host cell comprising a DNA vector, said DNA vector comprising a DNA construct, said DNA construct comprising a polynucleotide fragment having sequence as set forth in SEQ ID NO: 7, operably linked to a promoter.

In an embodiment of the present disclosure, there is provided a recombinant host cell comprising a DNA vector, said DNA vector comprising a DNA construct, said DNA construct comprising a polynucleotide fragment having sequence as set forth in SEQ ID NO: 8, operably linked to a promoter.

In an embodiment of the present disclosure, there is provided a recombinant host cell comprising a DNA vector, said DNA vector comprising a DNA construct, said DNA construct comprising a polynucleotide fragment encoding a synthetic polypeptide having sequence as set forth in SEQ ID NO: 3, operably linked to a promoter, said polynucleotide fragment sequence is as set forth in SEQ ID NO: 6.

In an embodiment of the present disclosure, there is provided a recombinant host cell comprising a DNA vector, said DNA vector comprising a DNA construct, said DNA construct comprising a polynucleotide fragment encoding a synthetic polypeptide having sequence as set forth in SEQ ID NO: 4, operably linked to a promoter, said polynucleotide fragment sequence is as set forth in SEQ ID NO: 7.

In an embodiment of the present disclosure, there is provided a recombinant host cell comprising a DNA vector, said DNA vector comprising a DNA construct, said DNA construct comprising a polynucleotide fragment encoding a synthetic polypeptide having sequence as set forth in SEQ ID NO: 5, operably linked to a promoter, said polynucleotide fragment sequence is as set forth in SEQ ID NO: 8.

In an embodiment of the present disclosure, there is provided a recombinant host cell comprising a DNA vector as described herein, wherein said host cell is of bacterial origin.

In an embodiment of the present disclosure, there is provided a recombinant host cell comprising a DNA vector as described herein, wherein said host cell is E. coli.

In an embodiment of the present disclosure, there is provided a recombinant host cell comprising a DNA vector as described herein, wherein said host cell is of fungal origin.

In an embodiment of the present disclosure, there is provided a recombinant host cell comprising a DNA vector as described herein, wherein said host cell is of plant origin.

In an embodiment of the present disclosure, there is provided a recombinant host cell comprising a DNA vector as described herein, wherein said host cell is of insect origin.

In an embodiment of the present disclosure, there is provided a method of obtaining a synthetic polypeptide as described herein, said method comprising: (a) obtaining a recombinant host cell comprising a DNA construct as described herein; (b) culturing said recombinant host cell under conditions conducive for expression of a synthetic peptide as described herein; and (c) isolating and purifying said synthetic peptide.

In an embodiment of the present disclosure, there is provided an elastomeric hydrogel comprising a synthetic polypeptide comprising "n" number of repeats of a sequence as set forth in SEQ ID NO: 1, covalently linked to at least one synthetic polypeptide.

In an embodiment of the present disclosure, there is provided an elastomeric hydrogel comprising a synthetic polypeptide comprising "n" number of repeats of a sequence as set forth in SEQ ID NO: 2, covalently linked to at least one synthetic polypeptide.

In an embodiment of the present disclosure, there is provided an elastomeric hydrogel comprising a synthetic polypeptide having sequence as set forth in SEQ ID NO: 3.

In an embodiment of the present disclosure, there is provided an elastomeric hydrogel comprising a synthetic polypeptide having sequence as set forth in SEQ ID NO: 4.

In an embodiment of the present disclosure, there is provided an elastomeric hydrogel comprising a synthetic polypeptide having sequence as set forth in SEQ ID NO: 5.

In an embodiment of the present disclosure, there is provided an elastomeric hydrogel comprising a synthetic polypeptide encoded by a polynucleotide fragment of sequence as set forth in SEQ ID NO: 6.

In an embodiment of the present disclosure, there is provided an elastomeric hydrogel comprising a synthetic polypeptide encoded by a polynucleotide fragment of sequence as set forth in SEQ ID NO: 7.

In an embodiment of the present disclosure, there is provided an elastomeric hydrogel comprising a synthetic polypeptide encoded by a polynucleotide fragment of sequence as set forth in SEQ ID NO: 8.

In an embodiment of the present disclosure, there is provided an elastomeric hydrogel comprising a synthetic polypeptide having sequence as set forth in SEQ ID NO: 3, encoded by a polynucleotide fragment of sequence as set forth in SEQ ID NO: 6.

In an embodiment of the present disclosure, there is provided an elastomeric hydrogel comprising a synthetic polypeptide having sequence as set forth in SEQ ID NO: 4, encoded by a polynucleotide fragment of sequence as set forth in SEQ ID NO: 7.

In an embodiment of the present disclosure, there is provided an elastomeric hydrogel comprising a synthetic polypeptide having sequence as set forth in SEQ ID NO: 5, encoded by a polynucleotide fragment of sequence as set forth in SEQ ID NO: 8.

In an embodiment of the present disclosure, there is provided a method of obtaining an elastomeric hydrogel as described herein.

In an embodiment of the present disclosure, there is provided a synthetic polypeptide as described herein, for use in preparing elastomeric hydrogels.

In an embodiment of the present disclosure, there is provided elastomeric hydrogel as described herein, for use in bio-medical applications.

In an embodiment of the present disclosure, there is provided elastomeric hydrogel as described herein, for use as bio-ink.

Although the subject matter has been described in considerable detail with reference to certain preferred embodiments thereof, other embodiments are possible.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

The examples as provided in the document describes in detail the synthesis of polypeptides and process for formation of hydrogels. The ability of the formed hydrogel to encapsulate various molecules has also been described along with the evaluation of cyto-compatibility of the hydrogel. The clones of all the three genes—SEQ ID NO: 6, SEQ ID NO: 7, and SEQ ID NO: 8 encoding polypeptides of SEQ ID NO: 3, SEQ ID NO: 4, SEQ ID NO: 5 respectively is described in this section. The results of formation of hydrogel has been shown with the polymer MODELAS1775-v2 (SEQ ID NO: 3).

Example 1

Design of Synthetic Polypeptides

The "MODELAS (Resilin-mimetic Modular Elasomer)" protein sequences (SEQ ID NO: 3, SEQ ID NO: 4, and SEQ ID NO: 5) contain a number of amino acid repeats, which upon reverse translation, according to codon bias, leads to repeats in the nucleotide sequence, causing difficulty in cloning due to polymerase slippage. SEQ ID NO: 3 refers to the protein sequence of MODELAS 1775-v2, SEQ ID NO: 4 refers to the protein sequence of MODELAS 1776, and SEQ ID NO: 5 refers to the protein sequence of MODELAS 1777. The nucleotide sequence in each case was optimized by modifying the nucleotide at the wobble position in each in-frame codon. Internal TATA boxes, chi-sites and ribosomal entry sites were deleted AT-rich or GC-rich sequence stretches were minimized. Repeat sequences and RNA secondary structures were avoided. RNA instability motifs, if any, were omitted. Cryptic splice sites were also avoided. Appropriate restriction sites were introduced for ease in cloning and two stop codons were introduced before the 3' restriction site.

Example 2

Cloning

Figure 1:
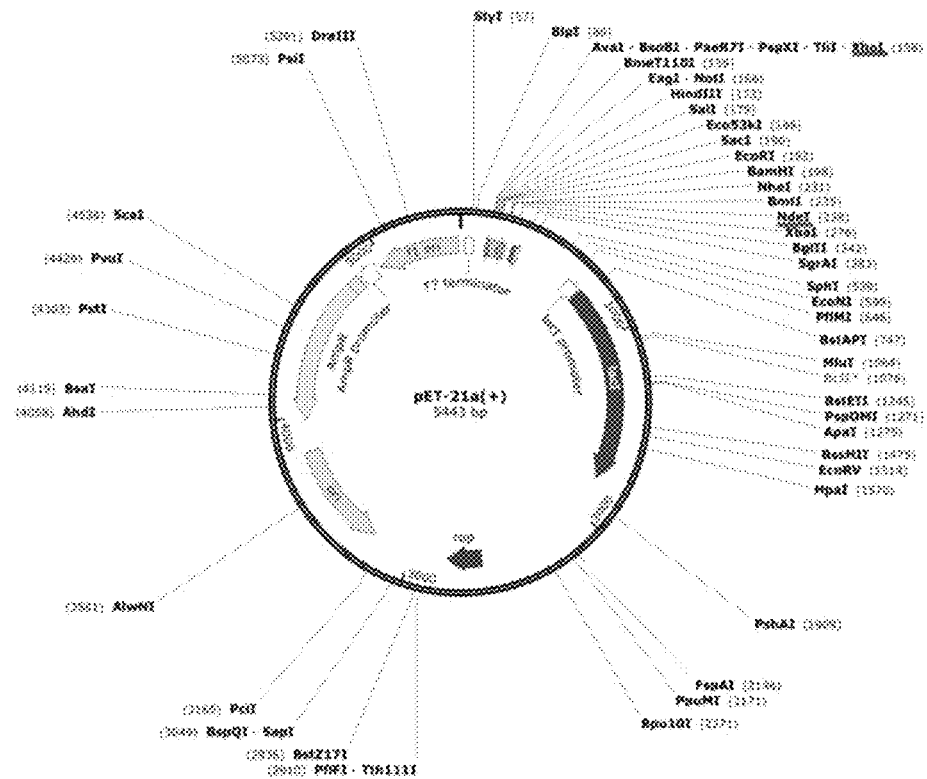
FIG. 1 depicts the vector map of pET21a, in accordance with an embodiment of the present disclosure.
Figure 2:
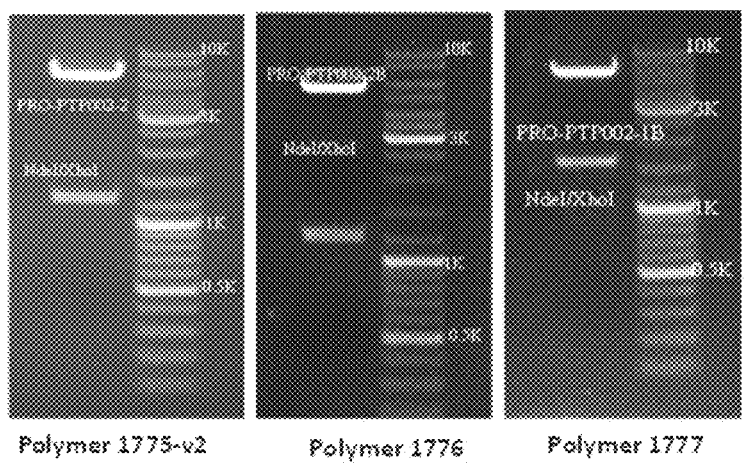
FIG. 2 depicts the restriction digestion analysis of clones, in accordance with an embodiment of the present disclosure.

The MODELAS genes (SEQ ID NO: 6, SEQ ID NO: 7, and SEQ ID NO: 8) obtained after reverse translation were synthesised and cloned into pET21a vector into the sites NdeI and XhoI (FIG. 1). The obtained clones were subsequently confirmed by restriction digestion using the enzymes NdeI and XhoI. FIG. 2 depicts the confirmation of positive clones in which the released inserts correspond to the size of respective genes. SEQ ID NO: 6 refers to the DNA sequence coding the protein represented by SEQ ID NO: 3 (MODELAS 1775-v2), SEQ ID NO: 7 refers to the DNA sequence coding the protein represented by SEQ ID NO: 4 (MODELAS 1776), and SEQ ID NO: 8 refers to the DNA sequence coding the protein represented by SEQ ID NO: 5.

Example 3

Expression and Purification of Polymer (1775-v2)

Following the cloning of the three genes, expression of the polymer 1775-v2 (SEQ ID NO: 3) was studied in detail with respect to the formation of hydrogels. The positive clone was expressed in BL21(DE3) cells using IPTG induction and expression was checked post 3 hours of incubation.

Figure 3:
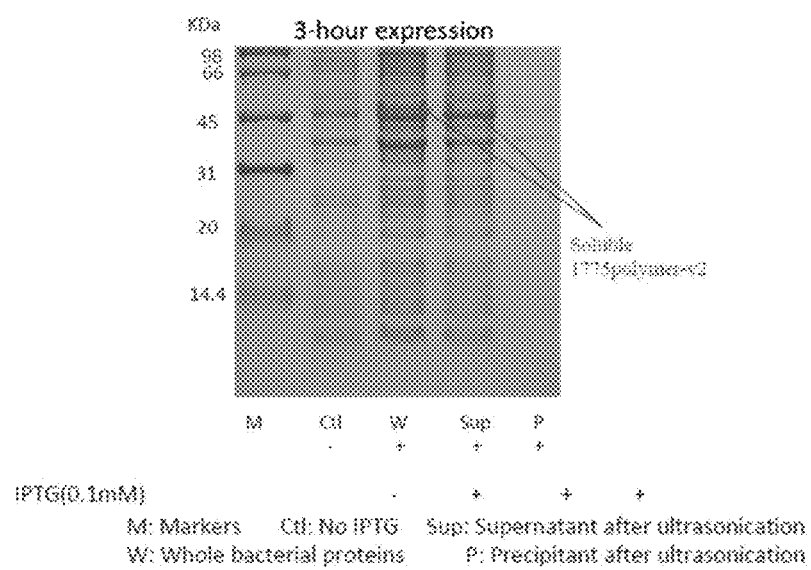
FIG. 3 depicts the expression of a polymer 1775-v2 (SEQ ID NO: 3) in BL21 cells 3 hours post IPTG induction, in accordance with an embodiment of the present disclosure.

FIG. 3 depicts the expression of a peptide comprising multiple number of repeats of SEQ ID NO: 1 in BL21 (DE3) cells 3 hours post induction. Cells were induced using IPTG. The bacterial lysate was fractionated on a SDS-PAGE gel and stained with Commassie blue stain.

Figure 4:
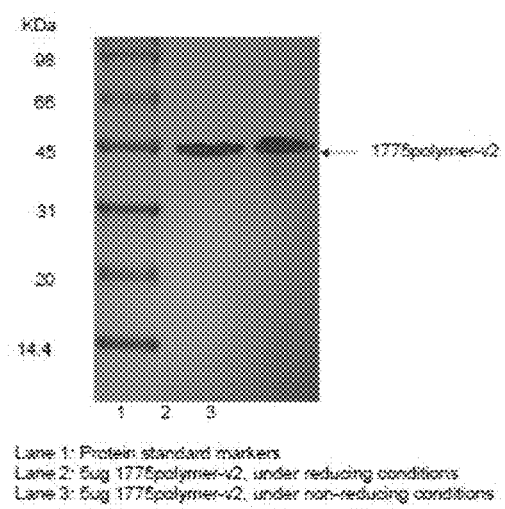
FIG. 4 depicts the purification of a polymer 1775-v2 (SEQ ID NO: 3) under reducing and non-reducing conditions, in accordance with an embodiment of the present disclosure.

FIG. 4 depicts the purification of said peptide under both reducing, and non-reducing conditions.

Example 4

Fabrication and Characterization of Elastomeric Hydrogels

After obtaining the purified form of the polymer as described in previous example, the experiment leading to fabrication of elastomeric gels using the polymer was performed.

The polymer 1775-v2 (comprising repeating units of peptide of SEQ ID NO: 1) was allowed to cross-link using RUBP at 0.1 mM as a photo-activated cross-linker and 5 mM APS as catalyst. The polymer cross links at the tyrosine residues forming di-tyrosine covalent bonds (FIG. 5A). FIG. 5A depicts self-assembly of peptide modules that brings the cross-linkable Tyrosine residues within the suitable distance of covalent bond formation. The blue fluorescence from the reaction well is a marker of di-tyrosine species formation. The di-tyrosines act as permanent network points of the polymer scaffold, while the hydrophilic sidechains of the peptide helps it to incorporate structural water to form the hydrogel (upto 99.2% water content).

The protein was used at increasing concentrations of 75 uM, 150 uM, 200 uM, 300 uM and 420 uM at various time points of 5 s, 20 s (FIG. 5B) for forming hydrogels. It can also be noticed that increased hydrogelation is observed with incremental polymer concentration.

The cross-linked product was run on the a 4-12% gradient gel (FIG. 5C). As can be seen from FIG. 5 C, besides the monomeric and dimeric forms of the polymer, there is also a significant amount of high molecular weight cross-linked product that does not enter the wells. Although formation of hydrogel is shown with only one polymer. It is contemplated that hydrogel can be formed independently with the polymer MODELAS1776 (SEQ ID NO: 4) and MODELAS1777 (SEQ ID NO: 5).

Example 5

Encapsulation of Various Cargo Molecules

The polymer 1775-v2 (comprising repeating units of peptide of SEQ ID NO: 1) was then tested to see if it is able to encapsulate small molecules such as sphero-beads and alexa fluor488. The polymer 1775v2 was allowed to cross-link in the presence of 0.1 mM RUBP and 5 mM APS with either sphero beads or alexa fluor. As can be observed from FIG. 6, the gel that formed was able to encapsulate both, the sphero beads (FIG. 6A) and alexa fluor (FIG. 6B).

Example 6

Cyto-Compatibility of Polymer

The polymer was evaluated for its cyto-compatibility using mouse muscle cells. The cross-linking was carried out using RUBP at 0.1 mM as a photo-activated cross-linker and 5 mM APS as catalyst along with cells. The cells were checked for encapsulation. As can be seen from FIG. 7A, all the cells are retained within the gel, suggesting that gel can be used to encapsulate and grow cells. FIG. 7B shows differential staining. Nucleus: DAPI (blue); Cytoplasm: (primary) Actin rabbit polyclonal (abcam), (secondary) anti rabbit 488 alexa flour (green).

Example 7

Hydrogel Preparation

Step 1: Simple Gelation Through Assembly of Peptides in Aqueous Solution:

1 mg of each peptide was dissolved in 100 μL of sterile dH$_2$O and dispensed in ELISA well plate/microbatch plate, with U/V shaped bottom. 80 μl of solution was dispensed in each ELISA well and kept for evaporation. Hydrogel formation started within 15 mins. Controlled evaporation at 25° C. in an incubator with the top of the wells covered with parafilm can also be carried out (few punctures are made on top of the parafilm and monitored periodically for a maximum of 30 minutes to an hour) for the excess water to be released and gels to set in.

Step 2: Photo-Crosslinking for Enhanced Gelation:

The peptide hydrogel was then covalently cross-linked using RuBP (Ruthenium Bipyridine) at 0.1 mM as a photo-activated cross-linker and 5 mM APS as catalyst. For this, once the simple gelation has set in for a maximum of 30 mins, the wells are exposed to 455 nm of light for about 2-5 minutes. This additional covalent cross-linking reduces the pore size of gel, and affects the release profile. The photo-exposure was performed in a custom-made irradiation chamber with 120 LEDs that give powerful cold blue light of 455 nm.

The present disclosure describes:
An efficient biopolymer that can form hydrogel with high water content (upto 99.2%).
Encapsulation of entities with varied dimensions ranging from nanometer to micron [small molecules (fluorophores)→macromolecules (antibody)→cells (stem cells)].
Bio-compatible gelation/encapsulation in blue light (455 nm).
Bio-compatible cross-linking using inherent tyrosine.
Porous extra cellular matrix mimetic scaffold.

Advantages of the Present Disclosure

The present disclosure provides a novel material for applications as a matrix in tissue engineering, regeneration and is compatible for photo-cured 3D printing. The design rationale for identifying building block, integration of the blocks following a modular design, formation of a hydrogel scaffold that mimics extra cellular matrix, incorporation of diverse 'cargo' encompassing small molecules to macromolecules to cells, resulting potential for applications in diverse area of tissue engineering, with applications for both outside (wound care) and inside body (tissue engineering implants) is disclosed. The polymer as disclosed herein is capable of self-assembly in presence of blue light (455 nm) and is a resilin-mimetic modular elastomer. The hydrogel as disclosed in the document is beneficial for use as matrix in case of chronic diabetic wound, and wounds in patients with compromised immunity systems due to age, malnutrition etc.; wherein there are big gaps between socio-economic needs and lack of available technological solutions.

We claim:

1. A synthetic polypeptide comprising the sequence of SEQ ID NO: 1 or SEQ ID NO: 2.

2. A synthetic polypeptide having the sequence of SEQ ID NO: 3, SEQ ID NO: 4, or SEQ ID NO: 5.

3. The synthetic polypeptide of claim 2, encoded by the polynucleotide sequence of SEQ ID NO: 6, SEQ ID NO: 7, or SEQ ID NO: 8.

4. A DNA construct comprising a polynucleotide fragment encoding the synthetic polypeptide of claim 1, operably linked to a promoter.

5. A DNA construct, comprising a polynucleotide fragment encoding a synthetic polypeptide having the sequence of SEQ ID NO: 3, SEQ ID NO: 4, or SEQ ID NO: 5, operably linked to a promoter.

6. The DNA construct of claim 5, wherein said polynucleotide fragment sequence is the sequence of SEQ ID NO: 6, SEQ ID NO: 7, or SEQ ID NO: 8.

7. A DNA vector comprising the DNA construct of claim 4.

8. A recombinant host cell comprising the DNA construct of claim 4.

9. The recombinant host cell of claim 8, wherein said host cell is of bacterial, plant, fungal, insect, or mammalian origin.

10. The recombinant host cell of claim 9, wherein said host cell is *E. coli*.

11. A method of obtaining a synthetic peptide, said method comprising:
 a) obtaining a recombinant host cell of claim 8;
 b) culturing said recombinant host cell under conditions conducive for expression of a synthetic peptide; and
 c) isolating and purifying said synthetic peptide.

12. An elastomeric hydrogel comprising the synthetic peptide of claim 2.

13. A method for preparing the elastomeric hydrogel of claim 12, said method comprising expression and purification of polymers and crosslinking of the polymers for preparing the elastomeric hydrogel.

14. A synthetic peptide of claim 1 for use in preparing the elastomeric hydrogels.

15. The elastomeric hydrogel of claim 12 for use in biomedical applications.

16. A synthetic peptide having the sequence of SEQ ID NO: 3, SEQ ID NO: 4, or SEQ ID NO: 5, for use in preparing the elastomeric hydrogels.

* * * * *